United States Patent [19]

Tyrode

[11] Patent Number: 5,245,875
[45] Date of Patent: Sep. 21, 1993

[54] PROCESS AND DEVICE FOR CHECKING CLOCK AND/OR JEWELLERY COMPONENTS

[75] Inventor: Alain Tyrode, Besancon Cedex, France

[73] Assignee: Societe de Fabrication Maty Sarl, France

[21] Appl. No.: 745,901

[22] Filed: Aug. 16, 1991

[30] Foreign Application Priority Data

Aug. 17, 1990 [FR] France .................. 90 10439

[51] Int. Cl.⁵ .................................. G01H 1/12
[52] U.S. Cl. .................................. 73/572; 73/579; 29/10; 63/26
[58] Field of Search ............ 73/572, 588, 579; 29/10; 63/26

[56] References Cited

U.S. PATENT DOCUMENTS

| | | | |
|---|---|---|---|
| 3,534,588 | 10/1970 | Schulz | 73/572 |
| 3,534,589 | 10/1970 | Gibbons et al. | 73/572 |
| 3,681,976 | 8/1972 | Schulz, Jr. | 73/572 |
| 5,090,244 | 2/1992 | Potier et al. | 73/572 |

FOREIGN PATENT DOCUMENTS

| | | |
|---|---|---|
| 3441805.9 | 5/1986 | Fed. Rep. of Germany . |
| 1276325 | 10/1961 | France . |
| 378243 | 7/1964 | Switzerland . |
| 1523295 | 8/1978 | United Kingdom . |

Primary Examiner—Hezron E. Williams
Assistant Examiner—Rose M. Finley
Attorney, Agent, or Firm—Davis, Bujold & Streck

[57] ABSTRACT

The process consists in subjecting the component to vibrations and detecting disturbances in the vibrations. The device for the application of this process comprises a vibrator (21) equipped with a swivelling clip (22) in which the component to be tested (23) is fixed. An accelerometer (34) fixed to the vibrating support (30) of the clip delivers an output signal to an electronic circuit which suppresses the low frequencies and which controls indicator lights indicating the acceptance or the refusal of the component. The position of the clip can be modified during the check.

19 Claims, 4 Drawing Sheets

PROCESS AND DEVICE FOR CHECKING CLOCK AND/OR JEWELLERY COMPONENTS

The present invention concerns a process for checking the attachment of an element added to a clock or other jewelry components, notably precious or semi-precious stones fitted by settings. According to the inventive process, these components are subjected to at least one series of vibrations. The resultant vibrations are picked up by means of a sensor, and the signals generated by the sensors are analyzed. These signals, as the case may be, are generated by shocks due to one or several poorly secured elements. A defected component is detected by noting the existence of disturbed signals generated by the sensor due to disturbed vibrations.

BACKGROUND OF THE INVENTION

One of the problems which arises from the manufacturing by craftsman, or on an industrial scale, of clock and/or jewelry components is that of the effective testing of the fixation or of the securement of the added elements, such as precious or semi-precious stones fitted by settings.

Patent CH-378243 describes a process for putting clock components to the test in the face of various outside disturbances. The checks are carried out on a rotary circular bench using several check points to test the behavior of a clock component subjected to certain conditions such as variations of the ambient pressure, shocks, vibrations, etc., are non-instantaneous and the effective measures are read individually by the operator who has a fixed position in relation to this bench.

Patent DE-3441805 describes a device for putting shock absorber sets to the test by enabling the metal lever attachments to be checked by applying vibrations at a set frequency and by comparing the resulting vibrations to the initial vibrations to detect any possible attachment defect.

There is thus, at the present time, no simple device enabling an effective checking of the fixation of added elements to clock and/or jewelry or other assembled components. More particularly, there is no device to check whether one or several precious or semi-precious stones, or other added elements, are properly or poorly set.

SUMMARY OF THE INVENTION

The present invention proposes to offset this drawback by providing a process for quick and effective testing, and to provide a device which is simple to use and economically constructed for the application of the process. With this aim, the process according to the invention is characterized in that the components are subjected to at least one series of vibrations. The frequency of these vibrations is determined according to the type of component to be tested and has a frequency which is variable between two predetermined limiting values.

According to the preferred embodiment of the invention, the components are subjected to at least one series of vibrations of the sinusoidal low frequency type. The resulting vibrations are picked up by a sensor that generates corresponding signals. The signals are then analyzed for disturbed signals that indicate the presence of a defectively attached component.

In the preferred embodiment, upon the detection of the defectively attached component an indicator system is activated. The indicator system advantageously comprises at least one indicator light.

According to an alternative embodiment the signals are displayed on a cathodic screen.

In order to check the components, they are fixed, preferably rigidly by means of a vibrating clip. Preferably, the clip is positioned in relation to the axle (axis) of the vibration so as to obtain maximum sensitivity of the sensor to the signals. According to an advantageous variant, the position of the clip is modified during testing.

According to the invention, the means for subjecting the components individually to the vibrations is arranged so as to generate at least one series of vibrations. The frequency of these vibrations is predetermined according to the type of component to be tested.

The sensor is preferably an accelerometer, and the means for subjecting the components individually to at least one series of vibrations advantageously comprises a vibrator arranged so as to generate sinusoidal low frequency vibrations. The device preferably includes an indicator system to report the presence of a defectively attached component. This indicator system advantageously comprises at least one visual device, such as an indicator light. According to another embodiment, the indicator system can comprise an acoustical device. According to another alternative embodiment, the indicator system comprises a screen for visually displaying the signals.

To hold the component, the device advantageously comprises a clip to attach the components to be tested. The clip preferably swivels in relation to the axle (axis) of the vibrations generated by the vibrator. The vibrator is preferably a cylindrical unit having a vibrating support joined thereto by a swivel connection upon which the clip is joined by a pivoting axle.

BRIEF DESCRIPTION OF THE DRAWINGS

The present invention can be better understood by referring to the following description, by way of example, and to the attached drawings in which.

DETAILED DESCRIPTION OF THE INVENTION

Figure 1:
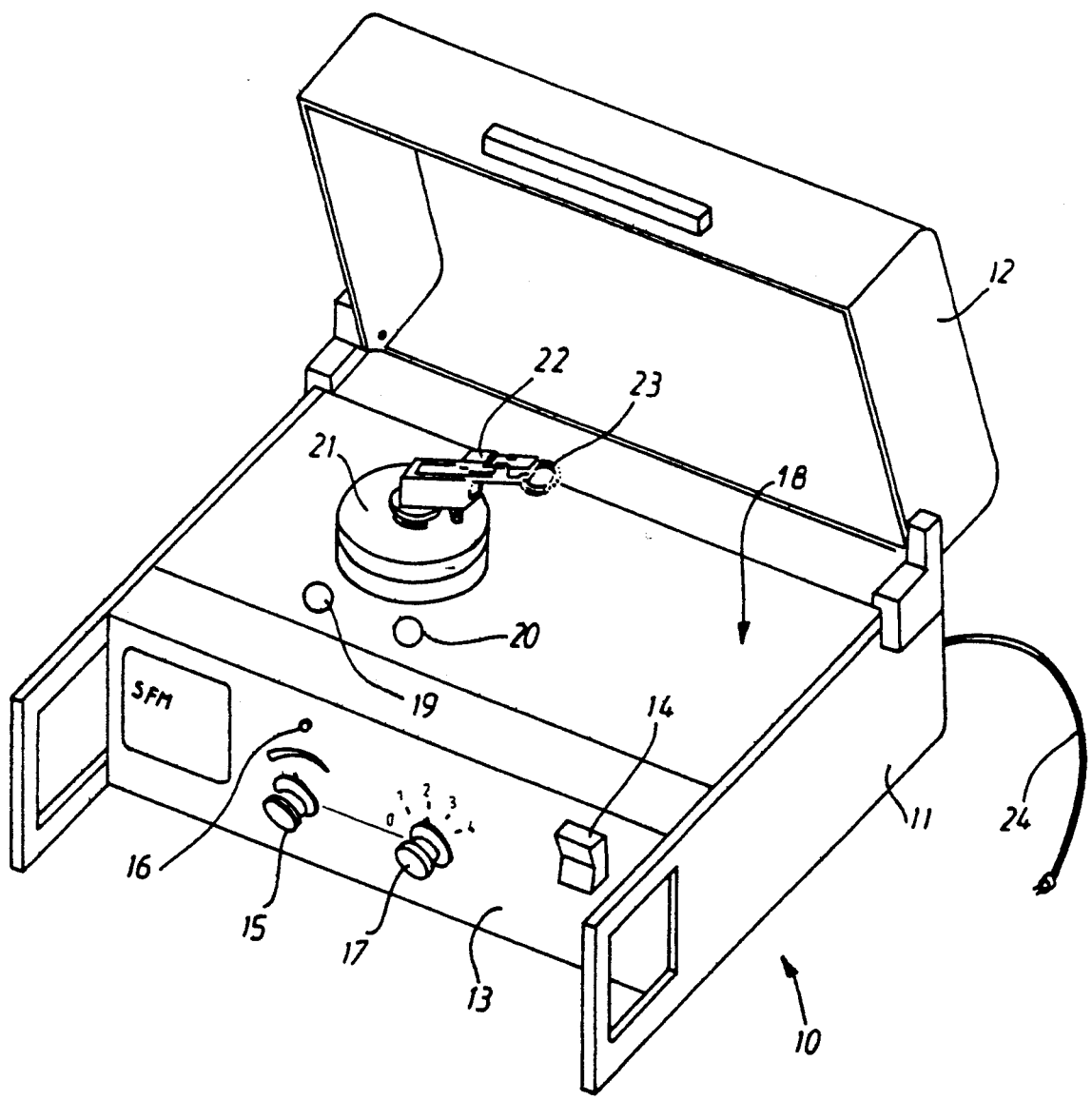
FIG. 1 shows an overall perspective view of the device according to the invention.

With reference to FIG. 1, the device shown is composed of a cabinet 10 made up of a base and a protective cover 12, inside which are fitted the components essential for operation of the device. On a front face 13 of the base 11 there is an on/off control switch 14, a calibration selector 15 connected to an indicator light 16 and a sensitivity selector 17.

On an upper face 18 of the base 11 of the device, there are two indicator lights 19 and 20 which constitute an indicator system to show a user whether the component is or is not defectively attached. This indicator system can also be replaced by a display (e.g. an accoustical display or visual cathodic display screen) D, integrated into the protective cover 12 on its inside or outside face, or used as a peripheral unit exterior to the device. The upper face of the base 18 also includes a vibrator 21 and a clip 22 for holding the component 23 to be tested (see FIG. 2). A power cord 24 enables the device to be plugged into a power source.

Figure 2:
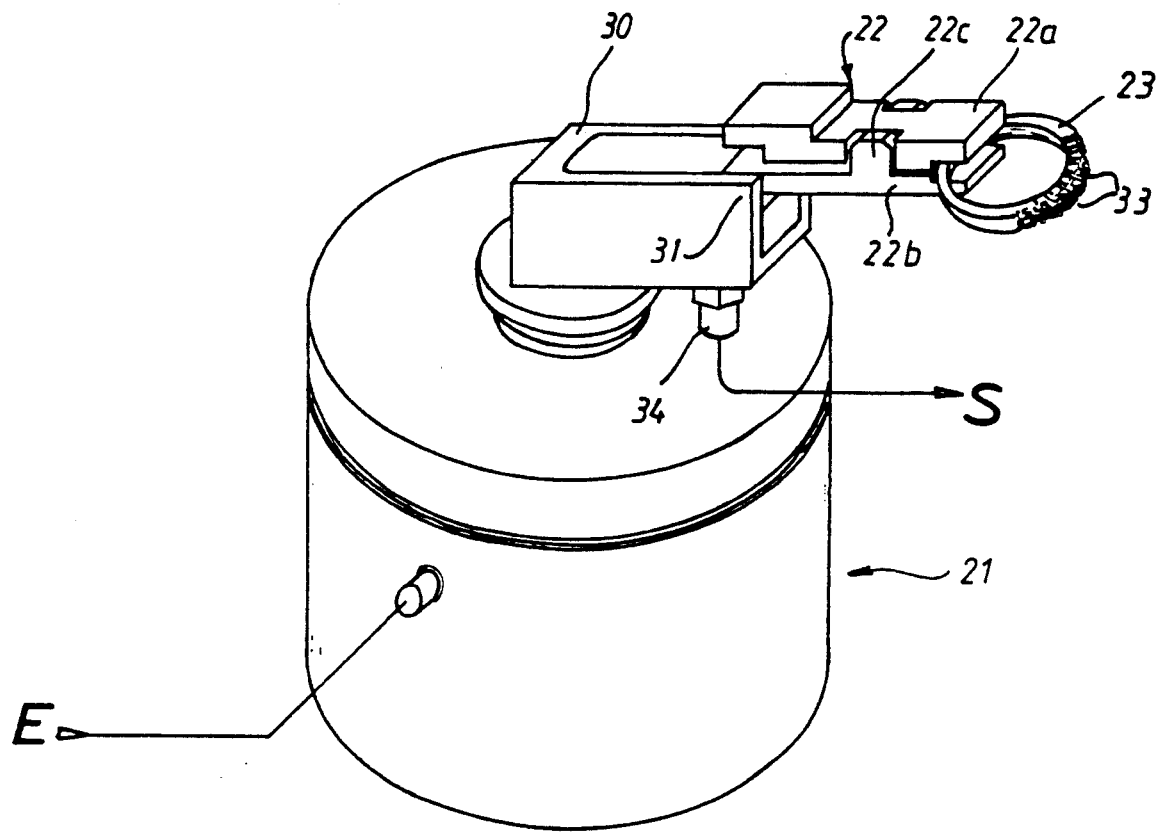
FIG. 2 shows an enlarged perspective view of one part of the device according to the invention.

FIG. 2 shows the vibrator 21 which is in the form of a cylindrical unit which comprises, at its upper extremity, a vibrating support 30 to which the clip 22 is attached. This clip is joined to the vibrating support 30 by means of a horizontal support or axle 31 which enables it to be positioned at different angles. The clip itself comprises two arms 22a and 22b articulated around the axle 22c, and which are arranged so as to firmly hold the component to be tested, such as a ring 23 to which are mounted stones or other set elements 33. An accelerometer 34, which constitute a vibration sensor, is fixed under the vibrating support 30.

The vibrator 21 and the accelerometer 34 are components which are readily available in the marketplace and sold, for example, by the company BRUESL AND KJAER. One suitable vibrator has the reference no. 4810 and has a low mass of around 18 g so that it is portable. The accelerometer, with a reference no. of 4375, also has a low mass, of around 2.4 g, and has a pass band of 16.5 khz.

Figure 3:
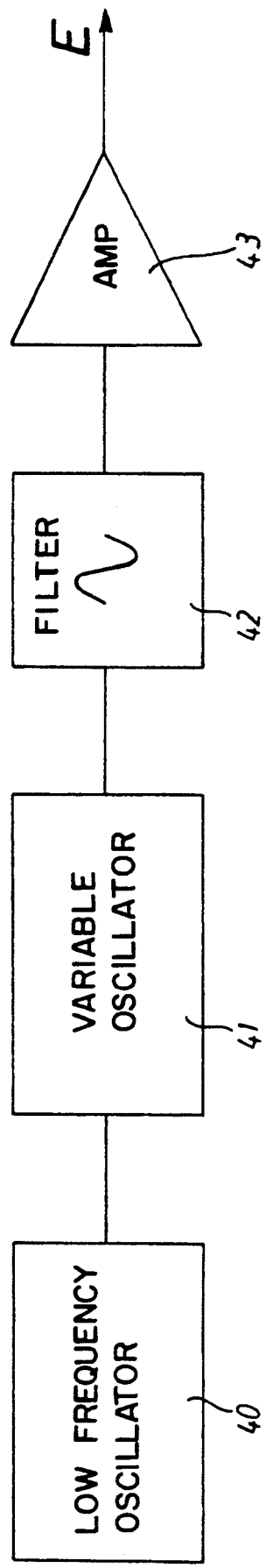
FIG. 3 is a schematic view of the part of the electronic circuit which permits vibrations to be generated.

FIG. 3 illustrates the vibrator excitation electronic circuit. It comprises a very low frequency (0.5 hz) oscillator 40 which generates a pilot signal at the frequency of 0.5 hz. This oscillator is coupled with an oscillator 41 which generates a pseudo sinusoidal signal of a variable frequency between 150 and 250 hz, the variation of which is controlled by the oscillator 40. A filter 42 produces a pure sinusoidal signal of the output signal of the oscillator 41. An amplifier 43 amplifies the output signal in order to obtain the power necessary to control the vibrator.

Figure 4:
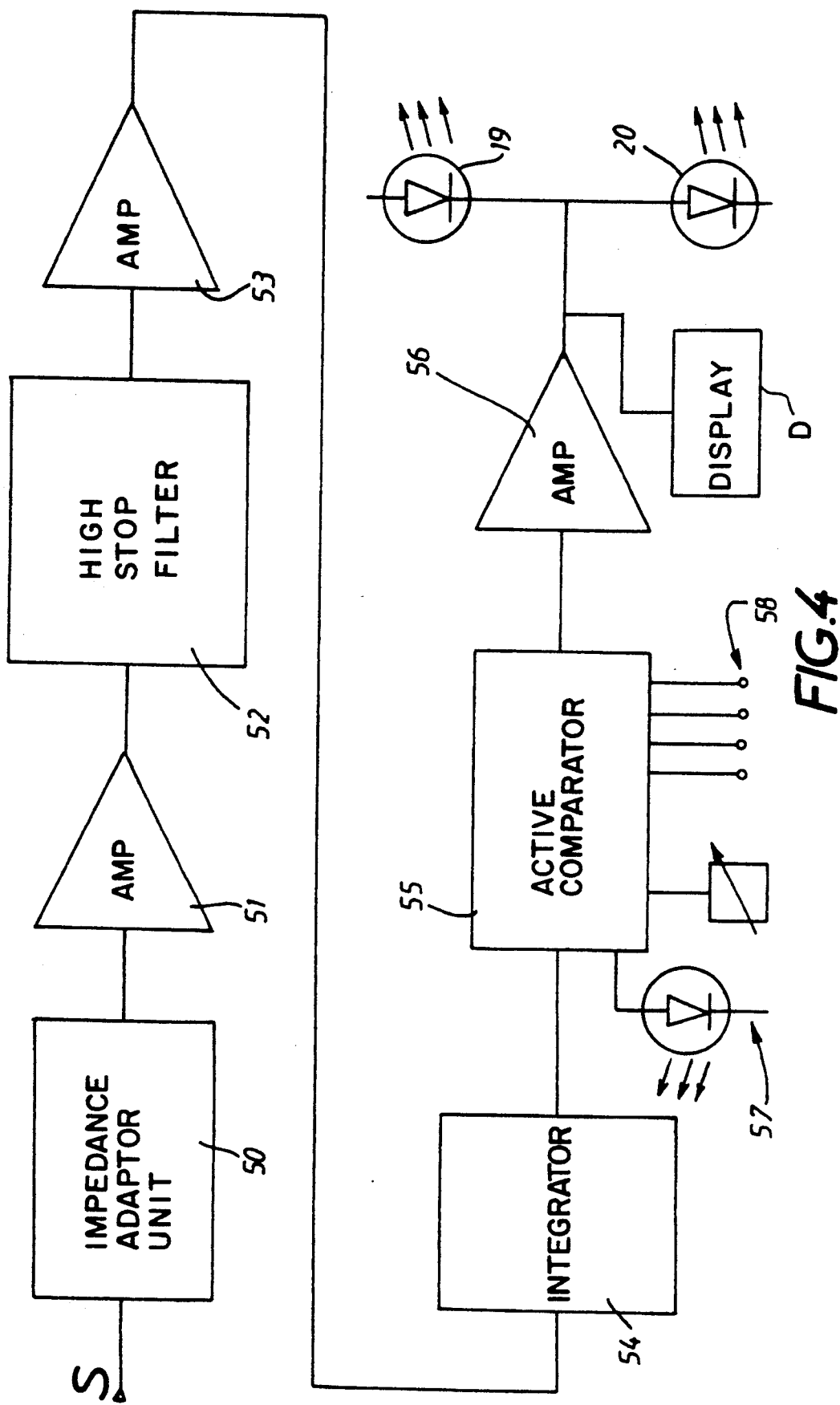
FIG. 4 is a schematic view of the part of the electronic circuit which permits the analysis to be carried out.

FIG. 4 illustrates the electronic measuring circuit which comprises an adapter-preaccentuator unit 50 which adapts the input impedance to that of the sensor, in this case the accelerometer, amplifies the high frequencies. An amplifier 51 amplifies the output signal of the adapter-preaccentuator 50. An active high stop filter 52 which suppresses the low frequencies of the signal, in particular the excitation frequency of the vibrator. A second amplifier 53 then amplifies in an adjustable way the alternating frequencies and eliminates the continuous component of the signal. An active integrator 54 then integrates the output signal of the amplifier 53 in order to generate a continuous signal:

$$V = -0.5 \int_{t_1}^{t_2} Ve\, dt.$$

An active comparator 55 then compares the output of the active integrator 54 to a selected control level. A third amplifier 56 is connected to the two indicator lights 19 and 20 so that its output amplifies the output signal of active comparator 55 to control the visualization of the results of the test through the indicator lights. One of the lights is, for example, green and emits a signal indicating that the component is not defectively attached. The other light can be red and reports a defective setting. An indicator lamp 57a and a calibrator 57b are coupled with the calibration control 15. The inputs 58 to the active comparator 55 are connected to the sensitivity selector 17.

In order to carry out a test by means of the device described above, the device is first connected to a supply of electricity, calibrated, and then the level of selection, i.e. the severity of the vibrations of the test, is chosen. During these operations, the component to be tested is not secured to the clip.

After these preliminary operations, components to be tested are place, one at time, into the clip.

This clip swivels in relation to the axis of the vibrations which is the vertical axis.

The installation and removal of the components can be carried out manually or automatically. In the latter case, the separation of the components which are not accepted from those that are acceptable can be carried out automatically.

For each type of component to be tested, a range of frequencies is preselected and the scanning of these frequencies is carried out to generate a series of vibrations to which said components are subjected. The limiting values are determined empirically and take into account, notably, the mass of the component and its shape.

The defectively attached components may be detected either by means of the indicator lights 19 and 20, or visually on the cathodic screen. When the screen is used, the generated signals can be analyzed in a more detailed way.

The invention is not limited to the above mentioned applications, but can be extended to all uses where the securement of a component is to be tested. The detection could also be carried out by an optical method, by picture analysis, or any other suitable means.

Wherefore I claim:

1. In a process for testing the securement of an element attached to a jewelry component, said process comprising the steps of:
    subjecting each said component to be tested, having at least one element attached thereto, individually to vibrations,
    sensing vibrational signals from said component to be tested with sensing means,
    analyzing the vibrational signals received by said sensing means, in which the received vibrational signals may including one or more disturbances from shock due to a poorly mounted element, to determine whether the at least one element is defectively attached to said component and detecting a defectively attached component by noting existence of a disturbance signal,
    the improvement wherein the step of subjecting each said component to be tested individually to vibrations comprises determining a frequency, according to the type of component to be tested, for at least a first series of vibrations and the frequency of said at least a first series of vibrations being variable between two predetermined limiting values.

2. A process according to claim 1, wherein the step of subjecting each said component to be tested individually to vibrations further comprising the step of using low frequency sinusoidal vibrations.

3. A process according to claim 1, wherein the step of analyzing the vibrational signal received by said sensing means further comprising the step of activating an indicator system to report the presence of a defectively attached component.

4. A process according to claim 3, wherein the analyzing step further comprising the step of activating at least one indicator light of the indicator system to report the presence of a defectively attached component.

5. A process according to claim 3, wherein the analyzing step further comprising the step of activating a visual display of the indicator system for detecting a defectively attached component.

6. A process according to claim 1, further comprising the step of securing, by means of a clip, each said component to be tested to a device for generating vibrations.

7. A process according to claim 6, further comprising the step of positioning said clip in relation to a vibrational axis of the vibrations so as to obtain maximum sensitivity of said sensing means to the vibrational signal received from said component to be tested.

8. A process according to claim 6, further comprising the step of modifying the position of said clip during testing.

9. In a device for testing the securement of an element attached to a jewelry component, said device comprising:
   means for subjecting each said component to be tested, having at least one element attached thereto, individually to vibrations,
   means for sensing vibrational signals from said component to be tested,
   means for analyzing the vibrational signals received by said means for sensing, in which the received vibrational signals may including one or more disturbances from shock due to a poorly mounted element, to determine whether the at least one element is defectively attached to said component, and means for detecting a defectively attached component by noting existence of a disturbance signal,
   the improvement wherein said means for subjecting each said component to be tested individually to vibrations comprises means for applying a frequency, according to the type of component to be tested, for at least a first series of vibrations and varying the frequency of said at least a first series of vibrations between two predetermined limiting values.

10. A device according to claim 9, wherein said means for sensing vibrational signals is an accelerometer.

11. A device according to claim 9, wherein said means for subjecting the component individually to vibrations comprises a vibrator positioned to generate low frequency sinusoidal vibrations.

12. A device according to claim 9, wherein said device further comprises at least one indicator to report the presence of a defective component.

13. A device according to claim 12, wherein said indicator to report the presence of a defective component comprises at least one visual display.

14. A device according to claim 13, wherein said at least one visual display is at least one indicator light.

15. A device according to claim 12, wherein said at least one indicator to report the presence of a defective component comprises at least one acoustical device.

16. A device according to claim 9, wherein said device further comprises a monitor for visualizing the vibrational signals.

17. A device according to claim 9, wherein said device further comprises a clip for securing said component to be tested to said device.

18. A device according to claim 11, wherein said clip is swivelable in relation to a vibrational axis of the vibrational signals so as to obtain maximum sensitivity of said clip to the vibrational signals.

19. A device according to claim 11, wherein said vibrator comprises a rigid cylindrical unit and a vibrating support connected to said cylindrical unit by a swivelable connection with the vibrating support carrying a clip.

* * * * *